(12) United States Patent
Dumoutier et al.

(10) Patent No.: US 6,359,117 B1
(45) Date of Patent: Mar. 19, 2002

(54) ISOLATED NUCLEIC ACID MOLECULES WHICH ENCODE T CELL INDUCIBLE FACTORS (TIFS), THE PROTEINS ENCODED, AND USES THEREFOR

(75) Inventors: Laure Dumoutier; Jamila Louhed; Jean-Christophe Renauld, all of Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/354,243

(22) Filed: Jul. 16, 1999

Related U.S. Application Data

(63) Continuation-in-part of application No. 09/178,973, filed on Oct. 26, 1998.

(51) Int. Cl.[7] .............................................. C07K 14/52
(52) U.S. Cl. ....................................... 530/351; 530/350
(58) Field of Search ................................. 530/350, 351

(56) References Cited

FOREIGN PATENT DOCUMENTS

| WO | 99/61617 | 12/1999 |
| WO | 00/65027 | 11/2000 |
| WO | 00/73457 A1 | 12/2000 |

OTHER PUBLICATIONS

Dumoutier et al PNAS 97(18):10144–10149, Aug. 2000.*
Doerks et al. TIG 14(6):248–250, 1998.*
Abaza et al. J. of Protein Chemistry 11(5):433–444, 1992.*
Parrish–Novak, et al., "Interleukin–21 and its receptor are involved in NK cell expansion and regulation of lymphocyte function," Nature 408:57–63 (Nov. 2, 2000).
Xie, et al., "Interleukin (IL–22), a Novel Human Cytokine That Signals Through the Interleukin Receptor–related proteins CRF 2–4 and IL–22R." J. Biol. Chem 275 (40):51335–51339 (Oct. 6, 2000).

* cited by examiner

*Primary Examiner*—David Saunders
*Assistant Examiner*—Amy DeCloux
(74) *Attorney, Agent, or Firm*—Fulbright & Jaworski, LLP

(57) ABSTRACT

The invention involves isolation of nucleic acid molecules, the expression of which are upregulated by interleukin-9. The amino acid sequences of the proteins which correspond to the nucleic acid molecules show some structural features of cytokines. In addition to the nucleic acid molecules and the proteins, various uses of the molecules are disclosed. The molecules are referred to as T cell inducible factors.

3 Claims, 1 Drawing Sheet

FIG. 1

Sequence homology between human and mouse TIF

```
SEQ ID NO:27  mTIF
SEQ ID NO:28  hTIF mTIF  MAVLQKSMSFSLMGTLAASCLLLLAIWAQEANALPVNTRC                                    40
       *  ***** *** *  *** *
hTIF  MAALQKSVSSFLMGTLATSCLLLLALLVQGGAAAPISSHC mTIF  KLEVSNFQQPYITVNRTFMLAKEASLADNNTDVRLIGEKLF                                   80
       ******* ***********************
hTIF  RLDKSNFQQPYITNRTFMLAKEASLADNNTDVRLIGEKLF mTIF  RGVSAKDQCYLMKQVLNFFTLEDVLLPQSDRFQPYMQEVVP                                   120
      **  **** * * *************
hTIF  HGVSMSERCYLMKQVLNFTLEEVLFPQSDRFQPYMQEVVP mTIF  FLTKLSNQLSSCHISGDDQNIQKNVRRLKETVKKLGESGE                                    160
        ** * * *  * * * ********
hTIF  FLARLSNRLSTCHIEGDDLHIQRNVQKLKCTVKKLGESGE mTIF  IKAIGELDLLFMSLRNACV                                                         179
      ****************** *
hTIF  IKAIGELDLLFMSLRNACI                                                         179
```

ISOLATED NUCLEIC ACID MOLECULES WHICH ENCODE T CELL INDUCIBLE FACTORS (TIFS), THE PROTEINS ENCODED, AND USES THEREFOR

RELATED APPLICATION

This application is a continuation in part of Ser. No. 09/178,973, filed Oct. 26, 1998, and incorporated by reference in its entirety.

FIELD OF THE INVENTION

This invention relates to newly isolated nucleic acid molecules and their uses. The nucleic acid molecules are shown to be unregulated by the cytokine interleukin-9 ("IL-9"). Also disclosed are the proteins encoded thereby. They are described as T Cell Derived Inducible Factors ("TIFs"). These nucleic acid molecules encode proteins which induce STAT activation in cells.

BACKGROUND AND PRIOR ART

The last decade has seen knowledge of the immune system and its regulation expand tremendously. One area of particular interest has been that of research on the proteins and glycoproteins which regulate the immune system. One of the best known families of these molecules are the cytokines. These are molecules which are involved in the "communication" of cells with each other. The individual members of the cytokine family have been found to be involved in a wide variety of pathological conditions, such as cancer and allergies. Whereas sometimes the cytokines are involved in the pathology of the condition, they are also known as being therapeutically useful.

Interleukins are one type of cytokine. The literature on interleukins is vast. An exemplary, but by no means exhaustive listing of the patents in this area includes U.S. Pat. No. 4,778,879 to Mertelsmann et al.; U.S. Pat. No. 4,490,289 to Stern; U.S. Pat. No. 4,518,584 to Mark et al.; and U.S. Pat. No. 4,851,512 to Miyaji et al., all of which involve interleukin-2 or "IL-2." Additional patents have issued which relate to interleukin-1 ("IL-1 "), such as U.S. Pat. No. 4,808,611 to Cosman. The disclosure of all of these patents are incorporated by reference herein. More recent patents on different interleukins include U.S. Pat. No. 5,694,234 (IL-13); U.S. Pat. No. 5,650,492 (IL-12); U.S. Pat. Nos. 5,700, 664, 5,371,193 and U.S. Pat. No. 5,215,895 (IL-11); U.S. Pat. Nos. 5,728,377, 5,710,251, 5,328,989 (IL-10); U.S. Pat. Nos. 5,580,753, 5,587,302, 5,157,112, 5,208,218 (IL-9); U.S. Pat. Nos. 5,194,375, 4,965,195 (IL-7); U.S. Pat. Nos. 5,723,120, 5,178,856 (IL-6), and U.S. Pat. No. 5,017,691 (IL-4). Even a cursory review of this patent literature shows the diversity of the properties of the members of the interleukin family. One can assume that the larger cytokine family shows even more diversity. See, e.g., Aggarwal et al., ed., Human Cytokines: Handbook For Basic And Clinical Research (Blackwell Scientific Publications, 1992), Paul, ed., Fundamental Immunology (Raven Press, 1993), pg 763–836, "T-Cell Derived Cytokines And Their Receptors", and "Proinflammatory Cytokines and Immunity." All cited references are incorporated by reference.

The relationships between various cytokines are complex. As will be seen from the references cited herein, as the level of a particular cytokine increases or decreases, this can affect the levels of other molecules produced by a subject, either directly or indirectly. Among the affected molecules are other cytokines.

The lymphokine IL-9, previously referred to as "P40," is a T-cell derived molecule which was originally identified as a factor which sustained permanent antigen independent growth of T4 cell lines. See, e.g., Uyttenhove et al., Proc. Natl. Acad. Sci. 85: 6934 (1988), and Van Snick et al., J. Exp. Med. 169: 363 (1989), the disclosures of which are incorporated by reference, as is that of Simpson et al., Eur. J. Biochem. 183: 715 (1989).

The activity of IL-9 was at first observed on restricted T4 cell lines, failing to show activity on CTLs or freshly isolated T cells. See, e.g., Uyttenhove et al., supra, and Schmitt et al., Eur. J. Immunol. 19: 2167 (1989). This range of activity was expanded when experiments showed that IL-9 and the molecule referred to as T cell growth Factor III ("TCGF III") are identical to MEA (Mast Cell Growth Enhancing Activity), a factor which potentiates the proliferative response of bone marrow derived mast cells to IL-3, as is described by Hültner et al., Eur. J. Immunol. and in U.S. patent application Ser. No. 498,182 filed Mar. 23, 1990, the disclosures of both being incorporated by reference herein. It was also found that the human form of IL-9 stimulates proliferation of megakaryoblastic leukemia. See Yang et al., Blood 74: 1880 (1989). Recent work on IL-9 has shown that it also supports erythroid colony formation (Donahue et al., Blood 75(12): 2271–2275 (Jun. 15, 1990)); promotes the proliferation of myeloid erythroid burst formation (Williams et al., Blood 76: 306–311 (Sep. 1, 1990); and supports clonal maturation of BFU-E's of adult and fetal origin (Holbrook et al., Blood 77(10): 2129–2134 (May 15, 1991)). Expression of IL-9 has also been implicated in Hodgkins's disease and large cell anaplastic lymphoma (Merz et al., Blood 78(8): 1311–1317 (Sep. 1, 1990). Genetic analyses of mice that were susceptible or resistant to the development of bronchial hyperresponsiveness have unraveled a linkage with the IL-9 gene as well as a correlation between IL-9 production and susceptibility in this model (Nicolaides et al., Proc. Natl. Acad. Sci. USA, 94, 13175–13180, 1997). Human genetic studies also point to the IL-9 and IL-9R genes as candidates for asthma (Doull et al., Am. J. Respir. Crit. Care Med., 153, 1280≧1284, 1996; Holroyd et al., Genomics 52, 233–235, 1998). Secondly, IL-9 transgenic mice allowed for the demonstration that increased IL-9 expression result in lung mastocytosis, hypereosinophilia, bronchial hyperresponsiveness and high levels of IgE (Temann et al., J. Exp. Med. 188, 1307–1320, 1998; Godfraind et al., J. Immunol. 160, 3989–3996, 1998; McLane et al., Am. J. Resp. Cell. Mol. 19:713–720 (1999). Taken together, these observations strongly suggest that IL-9 plays a major role in this disease.

IL-9 is known to affect the levels of other molecules in subjects. See Louahed et al. J. Immunol. 154: 5061–5070 (1995; Demoulin et al., Mol. Cell. Biol. 16: 4710–4716 (1996), both incorporated by reference. It will be recognized that the molecules affected have their own functions in biological systems. For example, Demoulin et al. show that many of the known activities of IL-9 are mediated by activation of STAT transcription factors. As such, there is continued interest in trying to identify molecules whose presence and/or level is affected by other molecules, such as cytokines.

The disclosure which follows describes such molecules. It was found that nucleic acid molecules encoding the proteins of the invention were expressed in the presence of IL-9, but not in its absence. Hence, these molecules are, inter alia, "markers" for the expression or effect of IL-9 in a subject. The molecules are referred to as T Cell Derived Inducible Factors or "TIFs" hereafter. These and other features of the invention will be seen in the disclosure which follows.

BRIEF DESCRIPTION OF THE FIGURES

FIG. 1 compares deduced amino acid sequences of murine and human TIF (SEQ ID NOS: 27 and 28, respectively).

FIG. 2 (10 pages), presents information in nucleotide sequences.

DETAILED DESCRIPTION OF PREFERRED EMBODIMENTS

EXAMPLE 1

The murine lymphoma cell line BW5147 is well known as a cell line which can be grown in vitro, without the need to add any cytokines to its culture medium. In order to identify genes induced by IL-9, samples of BW5147 were cultured either with (200 U/ml), or without IL-9, for 24 hours. Then, total RNA was isolated, using guanidium isothiocyanate lysis, and CsCl gradient centrifugation. These techniques are well known in the art. Following this, polyadenylated RNA was purified from the total RNA, by using an oligo(dT) cellulose column. The isolated, polyA RNA was then used to generate double stranded cDNA. A commercially available oligo(dT) primer was used. Anywhere from 3–5 ug of polyA RNA were heated to 70° C. for 10 minutes with 1 µg of oligo dT, and then incubated with 5× first strand buffer (250 mM HCl (pH 8.3), 375 mM KCl, 15 mM MgCl$_2$), 10 mM dithiothreitol, 500 uM of deoxynucleotide triphosphates, and 800 U of reverse transcriptase. Total volume of the reaction mixture was 20 ul, and the reaction was allowed to proceed at 37° C. for one hour. This resulted in synthesis of the first stand of cDNA. Second strand synthesis was accomplished by adding 30ul of 5 second strand buffer (100 mM Tris-HCl (pH 6.9)), 450 mM KCl, 23 mM MgCl$_2$, 0.75 mM β-NAD$^+$, 50 mM (NH$_4$)$_2$SO$_4$, together with 60 U of *E. coli* derived DNA polymerase I, 2 U of *E. coli* RNase H, 10 U of *E. coli* DNA ligase, and 250 uM of deoxynucleotide triphosphates, and brought to a final volume of 150 ul. The mixture was incubated for two hours, at 16° C.

The product was extracted using phenol-chloroform, and was precipitated with ethanol. The final cDNA product was then resuspended in 200 µl of TE.

These steps were carried out for both the stimulated BW5147 cells ("tester" hereafter), and for parallel, unstimulated BW5147 cells ("driver" hereafter).

EXAMPLE 2

The cDNA prepared in Example 1 was then subjected to subtraction cloning in accordance with well known methods. To do this, six oligonucleotides were prepared:
5'-AGCACTCTCC AGCCTCTCAC CGCA-3 (SEQ ID NO: 1);
5'-GATCTGCGGT GA-3' (SEQ ID NO: 2);
5'-ACCGACGTCG ACTATCCATG AACA-3' (SEQ ID NO: 3);
5'-GATCTGTTCA TG-3' (SEQ ID NO: 4);
5'-AGGCAACTGT GCTATCCGAG GGAA-3' (SEQ ID NO: 5); and
5'-GATCTTCCCT CG-3' (SEQ ID NO: 6).
These were used as explained herein. Double stranded cDNA (2 ug), was digested with restriction endonuclease DpnII, extracted with phenol-chloroform, precipitated with ethanol, and on resuspended in 20 ul of TE (10 mM Tris-HCl (pH 7.5); 1 mM EDTA). Twelve ul (1.2 ug), of cut cDNA was ligated to double stranded SEQ ID NOS: 1 and 2, in a mixture which included 4 ul of desalted SEQ ID NO: 1 (2mg/ml), 4 ul desalted SEQ ID NO: 2 (1 mg/ml), 10 µl of 5× adapter buffer (330 mM Tris-HCl, pH 7.6, 50 mM MgCl$_2$, 5 mM ATP), 7 µl DTT (100 mM), and 28 µl of H$_2$O). The oligonucleotides were annealed to each other and to the sample DNA by heating the mixture to 50° C. and then cooling it to 10° C. over one hour, followed by adding 5 ul of T4 DNA ligase, and incubation for 12–14 hours, at 12–16° C. The mixtures were diluted by adding 140 ul of TE. PCR was then carried out on 200 ul samples, as described infra.

EXAMPLE 3

To carry out PCR, 200 ul samples containing 2 ul of the ligation product in a buffer of 66 mM Tris-HCl, pH 8.8, 4 mM MgCl$_2$, 16 mM (NH$_4$)$_2$SO$_4$, 33 ug/ml BSA, 0.3 mM of each dNTP (concentration: 500 µM), and 2 ug of SEQ ID NO: 2 were first heated at 72° C. for three minutes to remove any of SEQ ID NO: 1 which was hybridized to the product of Example 2. The 3' ends were then filled in by using 5 U of Taq polymerase (5 minutes, 72° C.). Twenty cycles of amplification were carried out (1 cycle: 1 minute at 95° C., and three minutes at 72° C.), after which products were combined, phenol extracted, ethanol precipitated, and resuspended in TE buffer, at a concentration of 0.5 ug/ul. Hereinafter, this is referred to as the representation.

EXAMPLE 4

The representation was then prepared for subtractive hybridization by removing SEQ ID NO: 1 therefrom by digestion with Dpn II. The resulting digest was phenol extracted and ethanol precipitated. In the case of the unstimulated sample, this resulted in the driver, while the stimulated sample resulted in the tester. Portions of tester (20 ug) were gel purified on a 1.2% agarose gel and isolated. Samples (2 ug), were ligated to SEQ ID NOS: 3 and 4, in the same way that SEQ ID NOS: 1 and 2 were ligated, as described, supra.

In a first cycle of subtractive hybridization, 0.4 ug samples of tester with SEQ ID NOS: 3 and 4 ligated thereto were mixed with 40 ug of driver cDNA. The mixture was phenol extracted, ethanol precipitated, dissolved in 2 ul of 3×EE buffer (30 mM EPPS pH 8.0), 3 mM EDTA; pH 8.0, 3 mM EDTA. This was overlaid with 30 ul of mineral oil, and denatured for five minutes at 98° C. A 5M NaCl solution (0.5 ul) was added, and DNA was hybridized for 20 hours, at 67° C. The reaction mixture was diluted to 200 ul with TE, and tRNA carrier. The samples were incubated for three minutes at 72° C. to melt away SEQ ID NO: 4, and then four PCR reactions (200 ul) were prepared. These included 20 ul of diluted hybridization mix without primer, to fill in the ends of the reannealed tester, followed by 10 cycles of amplification after adding samples of SEQ ID NO: 3 (1 cycle: 1minute at 95° C, three minutes at 70° C.) after which products were combined, phenol extracted, ethanol precipitated, and resuspended in 40 µl of 0.2×TE buffer. Single stranded DNA was degraded by a 30 minute treatment of 20 µl of this material with 20 U of mung bean nuclease, at a total volume of 40 ul. Samples was diluted (1:5), in 50 mM Tris-HCl, at pH 8.9, followed by five minutes of heating at 98° C. to inactivate the enzyme. A second PCR was carried out, using 20 ul of the product described supra, 2 ul of SEQ ID NO: 3 (1 mg/ml), and 1 ul (5 U) of Taq DNA polymerase. A total of 18 cycles (1 cycle: 1 minute at 95° C., three minutes at 70° C.) were carried out. Products were combined, phenol extracted, ethanol precipitated, and resuspended at 0.5–1 ug/µl. The product is referred to hereafter as "DP1", or the first difference product.

EXAMPLE 5

DP1 was then digested with endonuclease DpnII, as described above, and was ligated to SEQ ID NOS: 5 and 6, following the same processes described for SEQ ID NOS: 1, 2, 3 and 4. Subtractive hybridization and selective amplification, as described in example 4, was repeated, and second difference product, or "DP2", was generated. In these experiments, 50 ng of DP1 was the tester. The driver (40 ug), was as described supra. The process was repeated to generate a third difference product, using SEQ ID NOS: 3 and 4 as adapters. To generate the third product, 100 pg of tester were mixed with 40 μg of driver. All steps of the protocols supra were repeated, except the final amplification was carried out for 22 cycles, where one cycle was one minute at 95° C., and three minutes at 70° C. This yielded the final difference product.

EXAMPLE 6

The final difference products were digested with DpnII, and then cloned into the BamHI site of a commercially available vector, i.e., ptZ19R. Double stranded DNA plasmids were prepared, and then sequenced, using standard methods. The sequences were compared to known sequences in the GenBank and EMBL data bases, using a BLAST search program.

At the end of this subtraction procedure, a short cDNA fragment was identified, i.e., a fragment about 200 base pairs long. This fragment was used to screen a cDNA library from BW 5147 cells. The largest clone was sequenced. It is discussed infra. It does not correspond to any known sequence.

The nucelotide sequence (SEQ ID NO: 7), is 1121 bases long, including a 537 base pair open reading frame, which encodes a protein 179 amino acids long. The predicted molecular weight of the protein is 20,093. There are two additional ATG codons which, if they acted as start codons, would produce proteins 172 and 167 amino acids in length, with molecular weights of 19,335 and 18,770 daltons, respectively. Each form of the protein is characterized by a sequence of hydrophobic amino acids which would be cleaved off of the molecule via the endoplasmic reticulum to provide a mature protein.

Analysis of the sequence shows three AT rich motifs (TTATTTAT). These motifs are rp often found in 5'-untranslated regions of cytokines and oncogenes. Kruys et al., Science 245: 852 (1989), have shown that these repeats modulate stability of mRNA for TIF.

EXAMPLE 7

The cDNA isolated and analyzed in example 6, supra, was then used as a probe to identify genomic DNA for TIFα.

A genomic library prepared from mouse strain 129 was screened with SEQ ID NO: 7, following standard methods. An EcoRI fragment from a positive clone was subcloned into plasmid pZERO and partially sequenced. The partial sequence is presented as SEQ ID NO: 8.

EXAMPLE 8

A second EcoRI fragment from the positive clone described in Example 7, supra, was also subcloned. There was a great deal of homology, but the sequences were not identical. To be specific, intron 1 of this sequence was 98% identical to SEQ ID NO: 8, intron 2 was 100% identical and intron 3 was 92% identical.

What is striking about the sequences is that the promoters are not at all homologous, suggesting independent regulation. The 5' untranslated regions are 92% identical. The first exon for TIFα is split into exon 1α and exon 1β. The first coding exon (which is exon 1b for TIFα and exon 1 for TIFβ) are 99.5% identical, while the second exons are 100% identical, the third exons 97% identical, the fourth exons 98.5% identical, and 96% for the fifth exon. In the untranslated 3'-region, homology is 96%.

EXAMPLE 9

Using the information described in example 8, supra, a cDNA sequence for the second clone, designated TIFβ was deduced, and is set forth as SEQ ID NO: 9. The genomic DNA sequence was also ascertained, in the same manner as is described, supra, and is set forth as SEQ ID NO: 29.

As compared to the coding region for TIFα, that of TIFβ has six silent changes. There are two changes which result in an inconsequential amino acid change (at both of positions 36 and 113, Val in TIFα) becomes Ile in TIFβ). There is also a more significant change, at position 112, where Gln becomes Arg.

EXAMPLE 10

Experiments were undertaken to study expression of the TIFs. BW 5147 cells were stimulated with recombinant murine IL-9 (200 U/ml), for varying periods of time (0.2, 0.5, 1, 2 & 24 hours). Total RNA was then isolated, using standard methods and reagents. Reverse transcription was then carried out, using 5 μg total RNA and an oligo (dT) primer. Samples of cDNA corresponding to 20 ng of total RNA were then amplified for 25 cycles using different primers. (One cycle was 4 minutes at 94° C., 1 minute at 57° C, and 2 minutes at 72° C.). The TIF primers were:
5'-CTGCCTGCTT CTCATTGCCC T-3' (SEQ ID NO: 10) and
5-CAAGTCTACC TCTGGTCTCA T-3' (SEQ ID NO: 11) (sense and antisense, respectively).

These correspond to nucleotides 106–126, and 764–784 of SEQ ID NO: 7, respectively. As a control, β-actin was amplified as well, for 18 cycles (first cycle: 4 minutes at 94° C., 1 minute at 60° C., 2 minutes at 72° C. Succeeding cycles were 1 minute at 94° C., 1 minute at 2 minutes at 72° C.).

Following amplification, post PCR products were analyzed on a 1 % agarose gel, and specific amplification was confirmed, following blotting, using internal radioactive probes. The probe for TIF was:
5'-GACGCAAGCA TTTCTCAGAG-3' (SEQ ID NO: 12)
the conditions and probes set forth were not specific for one or the other of the forms of TIF; however, the amplification product of TIFα contains a KpnI restriction site, while the restriction site for TIFβ does not. Digestion of the amplification products with KpnI indicated that most, if not all, of the TIF mRNA induced by IL-9 was TIFα, suggesting that the TIFα expression was induced rapidly via the IL-9. The mRNA for TIFα was detectable after 30 minutes of stimulation, and reached a plateau over a 1–24 hour time period.

EXAMPLE 11

Experiments were then carried out which showed that the induction of TIF mRNA by IL-9, described supra, does not require protein synthesis. In these experiments, total RNA was extracted from cells stimulated for 24 hours, as described in example 10, but with or without 10 μg/ml of a protein synthesis inhibitor, cycloheximide, for 4.5 hours. In a parallel set of to experiments, cells were not stimulated. The total RNA was extracted, and RT-PCR amplification was carried out as described in example 10. Post-PCR products were analyzed on an ethidium bromide-stained, 1% agarose gel. What was seen was that the induction by IL-9 still occurred when protein synthesis was blocked. Hence, the effect of IL-9 is a direct effect, not requiring the is synthesis of a protein mediator.

EXAMPLE 12

In these experiments, the role of STAT proteins in induction of TIF mRNA was studied on derivatives of the cell line BW5147. The first line, BWh9R, expresses wild type human IL-9 receptors. The line BW-Phe 116 is a transfectant with a single mutation (at position 116), which renders the receptor unable to activate STAT transcription factors. Still another cell line, BW-mut 6, has a mutation which renders the receptor unable to activate STAT5, while retaining the ability to activate STAT1 and STAT3. Finally, cell line BW-mut7 has a single mutation which renders the IL-9 receptor unable to activate STAT1 and STAT3, but which retains the ability to activate STAT5.

Cell stimulation, isolation of total RNA, reverse transcription and amplification of cDNA were all carried out as described in example 10 (Cells were stimulated for 24 hours. Both human and murine recombinant IL-9 were used). The PCR products were analyzed on an ethidium bromide stained, 1% agarose gel, as describe supra.

The analysis revealed that human IL-9 did not induce expression in BW-Phe 116, suggesting that STAT transcription factors are implicated. It was found that IL-9 induced TIF expression in the BW-mut6 mutant, but not the mut7 variant, suggesting that STAT1 or STAT3 are involved, but not STAT5.

EXAMPLE 13

The expression of TIF mRNA in normal mouse spleen cells was then studied.

Spleen cells from 10–12 week old Balb/c mice were cultured for 24 hours in control medium or the control medium supplemented with 20 µg/ml of LPS (which activates B lymphocytes and macrophages), or ConA (which activates T cells), or ConA plus 1% of a blocking antiserum against murine IL-9, with β actin being used as a control. Purification of RNA, RT-PCR analysis were carried out as described supra.

The data indicated that TIF is, at best, very weakly expressed in resting spleen cells, not induced by LPS, but strongly induced by ConA. Anti IL-9 antiserum did not affect induction by ConA, suggesting that its effect is not mediated by IL-9, or is mediated by other cytokines.

When the ConA activated spleen cells were analyzed using sequences of RT-PCR products, it was found that these cells were expressing TIFα predominantly, or exclusively.

EXAMPLE 14

Further experiments showed that TIF mRNA was expressed even in the absence of IL-9 induction.

Spleen cells from 5 week old FVB mice were enriched for T cells, using a nylon wool column. Then, the cells were stimulated for 24 hours in medium supplemented with ConA (a T cell activator), or PMA (which activates PKC in most cells), either with or without IL-9.

Total RNA was isolated using standard techniques, and then ten microgram samples were fractionated via electrophoresis on a 1.3% agarose gel containing 2.2M formaldehyde. The fractions were then transferred to a nitrocellulose membrane, labeled, and assayed in a hybridization assay following Van Snick, et al, J. Exp. Med. 169: 363 (1989), incorporated by reference.

The results indicated that the induction of TIF by ConA was not modified, and that IL-9 did not induce TIF RNA in PMA activated spleen cells.

EXAMPLE 15

The expression of TIF mRNA in various cell lines was tested. In these experiments, murine cell lines were stimulated for at least one day, with a particular cytokine. Specifically, 9T7 is a T cell lymphoma, which responds to IL-2, IL-4 or IL-9. Cell lines TS3 and TS6 are derived from T helper cell clones, and proliferate in the presence of either IL-2 or IL-9. MC9 and LI38 are mast cell lines, which proliferate in the presence of either IL-3 or IL-9.

Following stimulation, total RNA was prepared using standard guanidium isothiocyanate lyses, and CsCl gradient centrifugation.

The 9T7 line was then analyzed by Northern blotting, as described in example 14, while the other lines were assayed using RT-PCR analysis, as described supra.

It was found that IL-9 unregulated TIF expression in T helper cells and mast cells, while IL-2 and IL-3 did not. The 9T7 cell line, however, showed roughly the same level of expression, regardless of the cytokine, indicating that IL-9 is not mandatory for TIF expression.

EXAMPLE 16

The expression of TIF mRNA in B cell lines was then studied. The cell lines A20, 70Z/3, and BCL-1 are B cell leukemia cell lines which grow, in vitro, without cytokines. These cells were stimulated for 24 hours with IL-4 and IL-9 and total RNA was isolated, using standard methods. Expression was analyzed by RT-PCR which was carried out for 35 cycles, followed by blotting and hybridization, as described supra.

The results indicated that TIF expression is detectable in B cells, but is weakly unregulated at best in the presence of IL-9 and IL-4.

EXAMPLE 17

Experiments were then carried out to study expression of the inventive molecules in T helper cell lines. TS2 and TS1 are known T helper cell lines, derived from T helper cell clones, which proliferate in the presence of either IL-9 or IL-2 (TS2), and either IL-9 or IL-4 (TS1). Specifically, TS1 or TS2 cells were grown in the presence of the listed cytokines for at least 10 days, after which RNA was extracted using known methods. Expression of the molecules was studied via RT-PCR (35 cycles), using the protocols described supra. In TS1 cells both L-4 and IL-9 induce TIF expression, but IL-2 does not do so in TS2 cells.

EXAMPLE 18

Expression of TIF mRNA in various mouse organs were studied. Total RNA was prepared from liver, kidney, heart, brain, intestine, spleen, thymus, lung, muscle and bone marrow, using standard guanidium isothiocyanate methodologies and CsCl gradient centrifugation. Forty cycles of RT-PCR were carried out, using the protocols described supra. Strongest expression was found in thymus tissue, while less intense signals were found in brain tissue, and weaker expression in the remaining tissues.

EXAMPLE 19

The following experiments describe production of TIFα in 293-EBNA cells.

Complementary DNA for TIFA was described supra. It was subcloned into a commercially available expression vector pCEP-4, in operable linkage with a CMV promoter.

The resulting plasmids were transfected into 293-EBNA cells, using standard lipofectamine methods. Following transfection, the cells were incubated in a methionine free medium, supplemented with $^{35}$S labeled methionine, for 24 hours. Supernatant was harvested, and run on an acrylamide gel, followed by electrophoresis. The gel was then dried and exposed to autoradiography for 1 day. A control was then run by transfecting cells with the same plasmid, in which the cDNA was cloned in the antisense direction.

A heterogenous band of about 25–30 kilodaltons was found from the cells transfected with TIF in the sense direction. Any discrepancies between the predicted molecular weight, the actual molecular weight in the system, and the heterogeneity, can be attributed to glycosylation.

EXAMPLE 20

Further experiments were carried out to study production of TIFα in COS cells. Specifically, TIFα cDNA was subcloned into the plasmid pEF-BOS.puro described by Demoulin et al., supra, in operable linkage with the EF-1α promoter. The plasmid cDNA was transfected into COS cells, using the same lipofectamine method described supra. The cells were incubated in methionine free medium, supplemented with $^{35}$S methionine for 24 hours, after which supernatant was treated as described in example 20, supra. Again, a heterogenous band of 25–30 kilodaltons was observed, as well as an 18 kilodalton band, which probably represents a non-glycosylated form of the molecule.

EXAMPLE 21

In these experiments, it was discovered that TIF induces STAT activation in mesangial and neuronal cells. It is known that when cytokines activate STAT factors, the factors dimerize, move from cytoplasm to the nucleus, and bind to target sequences in promoters. The details of the experiments follow.

Transfected 293-EBNA cells as described supra were used following incubation in normal medium for 48 hours, as were supernatant from the controls, also described supra. Samples of a mouse kidney mesangial cell line, ("MES13" hereafter), and rat pheochromocytoma cell line, ("PC12" hereafter), were used. Cell samples (0.5×10$^6$) were stimulated for 5–10 minutes in the presence of 1% of supernatant. Nuclear extracts were then prepared, in accordance with Demoulin et al., Mol. Cell. Biol. 16: 4710 (1996), incorporated by reference. In brief, cells were washed with PBS and then resuspended in 1 ml of ice cold hypotonic buffer for 15 minutes. a (Buffer was 10 mM HEPES buffer, pH 7.5, with 10 mM KCl, 1 mM MgCl$_2$, 5% glycerol, 0.5 mM EDTA, 0.1 mM EGTA, 0.5 mM dithiothreitol, and 1 mM Pefabloc, 1 mM Na$_3$V$_4$, and 5 mM NF). Cells were then lysed by adding 65 μl of NP-40, followed by vortexing. Nuclei were pelleted, by vortexing for 30 seconds at 14,000 rpm, followed by extraction in buffer supplemented with HEPES (20 mM), glycerol (20%), and NaCl (420 mM). Nuclear debris was removed by centrifuging for 2 minutes. DNA binding activity was determined in accordance with Demoulin et al., supra, using a $^{32}$P labeled double stranded oligonucleotide called "GRR," which contains the STAT binding site of the FcγRI gene promoter, i.e.:

5' ATGTATTTCC CAOAAA-3' (SEQ ID NO: 13) and
5'-CCTTTTCTGG GAAATAC-3' (SEQ ID NO: 14)
corresponding to the upper and lower strands of the binding sites in the GRR probe. Briefly, 5 μl volume of nuclear extracts were incubated in binding buffer (12 mM HEPES, pH 7.6, 10 mM KCl, 0.5 mM EDTA, 2.5% glycerol, 0.1 mg of poly(dI-dC) per ml) for 5 minutes. Radiolabeled GRR probe (10$^5$cpm; approximately 0.5 ng) was added, and incubation was continued for 25 minutes before loading onto a non-denaturing polyacrylamide gel.

It was also noted that the complexes observed in MES13 cells, described supra, were partially overshifted by both anti-STAT5 and anti-STAT3 antibodies, showing that (i) the cells under examination were targets for TIF, and (ii) that STAT3 and STAT5 are major components of the complex activated by TIF. The difference in STAT profile, as compared to the profile in Example 12, supra, is attributable to the difference in cell source (human versus mouse).

EXAMPLE 22

This example details the isolation and cloning of a nucleic acid molecule which encodes human TIF. First, human peripheral blood mononuclear cells were prepared via standard density gradient centrifugation. Following this preparation, samples were cultured for 24 hours, at 3×10$^6$ cells/ml, either with or without anti-CD3 monoclonal antibody (The antibody was the commercially available OKT3 mAb, used in the form of ascites fluid at 1/500 dilution). This antibody was used because T cell derived cytokines are generally expressed only upon activation by e.g., CD3 specific antibodies.

Total RNA was isolated from these cells, using standard guanidine-isothiocyanate/CsCl ultra-centrifugation techniques. Following isolation, 10 μg samples of the RNA were reverse transcribed using an oligo (dT)15 primer.

Following preparation of cDNA, as outlined supra, samples which corresponded to 100 ng of total RNA were amplified, via PCR, using the following primers:
5'-AGCTGCTCAA CTTCACCCTG GA-3' (SEQ ID NO: 15)
b 5'-CCACTCTCTC CAAGCTTTTT CA-3' (SEQ ID NO: 16)
which are based upon a murine cDNA sequence, (i.e., SEQ ID NO: 7). The PCR conditions involved 30 cycles of amplification, with one cycle defined as 1 minute at 94° C., followed by 1 minute at 42° C., and then 2 minutes at 72° C. Amplification product was separated on an agarose gel, using standard methods, and then sequenced. The result indicated that fragments of the cDNA had been amplified. Hence, a second reaction was carried but, using the same materials except SEQ ID NO: 16 was replaced by SEQ ID NO: 17, i.e.:
5'-CAAGTCTACC TCTGGTCTCA T-3'
This second PCR reaction was carried out for 25 cycles, with one cycle being defined as 1 minute at 94° C., followed by 1 minute at 45° C., and then 2 minutes at 72° C. The amplification product was subjected to the same steps as the first one. Again, fragments of cDNA were amplified.

EXAMPLE 23

Following preparation of amplification product, the 5' end of cDNA was isolated by using standard, 5'-RACE techniques. In brief, first strand cDNA was prepared by using SEQ ID NO: 18 as a primer, i.e.:
5'-TGGCCAGGAA GGGCACCACC T-3'
This primer was based upon the sequence information obtained in accordance with example 22. In brief, the 5'-RACE method was carried out by combining 1 μg of total RNA, prepared as described supra, 2.5 pmoles of SEQ ID NO: 18, reverse transcriptase , reverse transcriptase buffer, 2.5 μl of dNTP mix (10 mM), 2.5 μl of MgCl$_2$ (25 mM), and 2.5 μl of dithiothreitol (0.1 M). The reaction was carried out and, after completion, original RNA was removed via adding RnaseH, and Rnase TI. Any unincorporated dNTPs, as well as primer and proteins, were removed. The cDNA was tailed using terminal transferase, or "TdT." This enzyme creates a 3'-binding site for the abridged anchor primer, as described infra. Tailing was carried out by combining the purified, first strand cDNA, TdT, buffer (10 mM Tris-HCl, 25 mM KCl, 1.5 mM MgCl2), and 200 μM of dCTP.

Following the tailing reaction, PCR was carried out using 5'-TGGCCAGGAA GGGCACCACC T-3' (SEQ ID NO: 19), and 5'-RACE abridged anchor primer:
5'-GGCCACGCGT CGACTAGTAC GGGIIGGGIIGGGIIG-3' (SEQ ID NO: 20).
The amplification involved 35 cycles (1 cycle defined as 1 minute at 94° C., 1 minute at 56° C., and 2 minutes at 72° C.). Following this, nested amplification was performed on 5 μl of a 1/100 dilution of the amplification product, using SEQ ID NO: 19 and the abridged universal amplification primer:
5'-GGCCACGCGT CGACTAGTAC-3' (SEQ ID NO: 21). Amplification involved 30 cycles (1 cycle being defined as 1 minute at 94° C, 1 minute at 56° C, and 2 minutes at 72° C). The resulting PCR product was cloned, following standard procedures, and sequenced.

These three protocols, i.e., the two experiments described supra which generated fragments, and the 5'-RACE PCR, also described supra, permitted alignment of the sequenced amplification product, to generate the complete sequence.

Following the alignment, oligonucleotides were generated which flanked the deduced open reading frame, i.e.:
5'-CCTTCCCCAG TCACCAGTTG-3' (SEQ ID NO: 22) and
5'-TAATTGTTAT TCTTAGCAGG-3' (SEQ ID NO: 23).
These primers were used to amplify the entire open reading frame, using mRNA from CD3 specific mAb stimulated cells, as described supra. For amplification, 25 cycles (1 cycle being defined as 1 minute at 94° C., 1 minute at 56° C., and 2 minutes at 72° C.).

The complete sequence of the human cDNA is set forth at SEQ ID NO: 24.

As with the murine sequence, there are potential start codons at positions of SEQ ID NO: 24 which correspond to amino acids 1 and 13, as well as codons corresponding to methionine at amino acid positions 58, 85, and 92. The possible initiator codons correspond to proteins with calculated molecular weight of 19,998 daltons, and 18,735 daltons respectively (for 176 or 167 amino acids, respectively). As with the murine form of the protein, hydrophobic leader sequences are seen, indicating an N-terminal signal sequence of from about 20 to about 40 amino acids.

EXAMPLE 24

These experiments detail work on the isolation of human genomic DNA corresponding to the cDNA discussed supra.

Based upon the cDNA sequences, primers were developed which correspond to nucleotides 51–70 and the complement of nucleotides 631–650 of SEQ ID NO: 24. PCR was carried out, 103 using standard methodologies. Specifically, 100 ng of genomic DNA was used as a template, and 33 cycles of amplification were cararied out (one cycle of amplification being defined as 94° C. for 30 seconds, 50° C. for 30 seconds, and 72° C. for 5 minutes).

Once a sequence was isolated, it was sequenced, and this is set forth as SEQ ID NO: 25. The sequence is about 4.8 kilobases in length, and is believed to contain the entire genomic sequence encoding the TIF molecule, lacking only the 5' flanking region, the promoter, and the 3' end.

EXAMPLE 25

It was of interest to identify where the genomic DNA discussed supra was located in the human genome. In order to do this, two different approaches were taken. In the first, the sequence discussed supra, i.e., SEQ ID NO: 25, was labeled with a fluorescent label, and then was used to probe the human genome via fluorescent, in situ hybridization ("FISH") using standard methods.

In a second approach, a panel of radioactive hybrid clones were screened using the probe consisting of nucleotides 51–70 of SEQ ID NO: 24, and 5'-ATCAGATGGA TTACTGAATG-3' (SEQ ID NO:26). PCR was carried out using 25 ng of genomic DNA as a template, for 35 cycles, where one cycle is defined as 94° C. for in minute, 55° C for i minute and 72° C. for 2 minutes.

Both methodologies indicated that the gene is located at chromosome 12q15. Some work links diseases associated with asthma at this site. See, e.g. Nat. Genet. 15:389–392 (1997); Ober, fiDg et al, Hum. Mol Genet. 7(9):1393–1398 (1998); Nickel, et al, Genomic 46(1):159–162(1997); Takahashi, et al, Genomics 44(1):150–2(1997); Barnes, et al, Genomics 37(1):41–50(1996), all incorporated by reference..

EXAMPLE 26

These experiments describe the manufacture of antibodies which bind to the TIF protein. To make these, a peptide consisting of amino acids 40–61 encoded by SEQ ID NO: 7 was coupled to KLH carrier protein, using standard methods and a ratio of 1 mg peptide to 1 mg carrier protein. Subject animals (rabbits), were immunized 3 times, at 2 week intervals, with 150 μg of the complex. The immunogen was emulsified in Complete Freund's Adjuvant for the first injection, and then Incomplete Freund's Adjuvant for the next two.

A first bleed was performed one month after the last injection, and serum was prepared, following known methods.

The serum was then tested in a standard Western Blot. In brief, 10 μl of supernatant from cells transfected with SEQ ID NO: 7 were separated via SDS-PAGE electrophoresis, and then blotted onto PVDF membranes. Antiserum was diluted to 1:500, and used in a standard Western Blot protocol, together with anti-rabbit antibody as the secondary antibody, and a commercially available detection kit.

It was found that the serum did, in fact, recognize the TIF protein.

In FIG. 1, the deduced amino acid sequences of murine and human TIF are set out. The high degree of homology is seen in the boxed regions.

The foregoing examples describe the invention, one aspect of which are isolated nucleic acid molecules, which encode TIF proteins such as those with the amino acid sequence of the protein encoded by the nucleotide sequence of SEQ ID NO: 7, 24 or 25. It will be appreciated by one of ordinary skill that the degeneracy of the genetic code facilitates the preparation of nucleic acid molecules which may not be identical to the nucleotide sequence of SEQ ID NO: 7, 24 or 25, but which encode the same protein. Of course, SEQ ID NOS: 7, 24 and 25 are preferred embodiments of this invention, but other embodiments are also a part of the invention. Genomic DNA, complementary DNA, and RNA, such as messenger RNA, are all to be included therein. Isolated nucleic acid molecules from other animal species, including other mammals, are also a part of the invention. A preferred aspect of the invention are isolated nucleic acid molecules whose complements hybridize to SEQ ID NO: 7, SEQ ID NO: 8, SEQ ID NO: 9, or SEQ ID NO: 24 under stringent conditions. "Stringent conditions," as used herein, refer, for example, to hybridization at 65° C. in buffer (3.5×SSC), 0.02% Ficoll, 0.02% polyvinylpyrrolidone, 0.02% bovine serum albumin, 25 mM $NaH_2PO_4$ (pH 7), 0.1% SDS, 2 mM EDTA, followed by a final wash at 2×SSC, room temperature and then 0.1×SSC/ 0.2>SDS at temperatures as high as, e.g., about 65° C. More stringent conditions, such as 0.1×SSC, can also be used. These nucleic acid molecules encode proteins of about 17–22 kD as determined by SDS - PAGE, which activates STAT proteins, such as STAT 1, STAT3 and/or STAT5. In glycosylated form, these proteins can range from about 17 to about 30 kilodaltons, as determined by SDS-PAGE.

Also a part of the invention are expression vectors which include the nucleic acid molecules of the invention, operably linked to a promoter, so as to facilitate expression of the DNA. It is well within the skill of the artisan to prepare such vectors.

The vectors, as well as the nucleic acid molecules per se, can be used to prepare recombinant cells, be these eukaryotic or prokaryotic, wherein either an expression vector or the TI nucleic acid molecule itself is incorporated therein. *E. coli* cells, COS cells, CHO cells, etc., are all examples of types of cells which may be used in accordance with this aspect of the invention.

Proteins encoded by the above referenced nucleic acid molecules, preferably in isolated form, are another feature of this invention. By "protein" is meant both the immediate product of expression of the nucleic acid molecules, glycosylated forms of it, as well as multimeric forms, such as dimers, trimers, and so forth. Also a part of the invention are multimers, such as dimers, which contain at least one protein molecule of the invention, and at least one, different protein molecule. Preferably, this different protein molecule is a cytokine, such as IL-10. Also included as a feature of the inventions are constructs, such as fusion proteins, where all or a part of the proteins described supra are linked in some fashion, such as in a fusion protein, to at least one additional protein or peptide, or amino acid sequence. The "fusion partner" may be, for example, a molecule which provides a recognizable signal, either directly or indirectly, such as a FLAG peptide, β-galactosidase, luciferase, and so forth. These fusion partners are preferably joined to the molecule which is described supra at the N- and/or C- terminus of the protein; however, it is to be understood that there are many techniques known for joining molecules to amino acids, and any and all of these methodologies can produce constructs which are a part of the invention.

The individual protein molecules of the invention, as noted supra, will preferably have a molecular weight of from about 17 to about 30 kilodaltons, as determined by SDS-PAGE. In multimeric forms, the molecular weight of the complex will, of course, vary, but the TIF molecules contained therein will each have a molecular weight of about 17 to 30 kilodaltons, as determined by SDS-PAGE.

The proteins preferably consist of at least about 120 and no more than about 200 amino acids. Preferably, the amino acids sequences consists of or comprises all or part of the amino acid sequences encoded by SEQ ID NOS: 7,8, 9, 24 or 25. More preferably, the amino acid sequence contains all but about the first 40 amino acids encoded by said SEQ ID's. Even more preferably, it contains all but about the first 20 amino acids encoded by these sequences. Most preferably, the protein comprises amino acids set forth at SEQ ID NO: 27 or 28.

It will be appreciated by the skilled artisan that the proteins encoded by the above recited nucleic acid molecules are a feature of the invention, and may be used to produce antibodies, in accordance with standard protocols. Such antibodies, in monoclonal and polyclonal form, constitute a further feature of the invention as do fragments of said antibodies, chimeric forms, humanized forms, recombinant forms, and so forth. Also a feature of the invention are immunogens, comprising all or a part of the amino acid sequence protein molecules of the invention, preferably combined with an adjuvant, such as Complete or Incomplete Freund's Adjuvant. Portions of the protein sequences may be linked to other molecules, such as keyhole limpet hemocyanin, to render them more immunogenic. These antibodies can be used, e.g., to determine if the proteins of the invention are present. This is a further feature of the invention, as is now explained. It has been shown, in the examples, that the nucleic acid molecules of the invention were expressed in the presence of the IL-9. Hence, a further feature of the invention is a method to determine if IL-9 is or has been present, wherein one detects either the proteins of the invention, using antibodies for example, or mRNA using the nucleic acid molecules of the is invention, as probes. The mRNA can be determined directly, or in the form of cDNA. Such probes may or may not be labeled, as a matter of choice for the user. Hence, one can determine, for example, if, following administration of IL-9, the cytokine is still efficacious, by determining if the nucleic acid molecule of the invention is present. This type of assay can be adapted, for quantitative studies, wherein one determines, for example, either if a cell is sensitive to IL-9, and if so, how sensitive it is. One can also use the proteins of the invention to phosphorylate STAT proteins such as STAT1 , STAT3 and/or STATA 5. This in turn results in dimerization of the STAT protein, followed by migration to the nucleus to provoke the effect that these STAT proteins have on cells.

One could also use these molecules to test the efficacy of IL-9 agonists or antagonists when administered to a subject, such as a subject suffering from lymphoma, an immune system disorder such as an allergy, acquired immune deficiency syndrome, autoimmune diabetes, thyroiditis, or any of the other conditions described in, e.g, U.S. Pat. Nos. 5,830,454; 5,824,551, and pending application Ser. No. 08/925,348, filed on Sep. 8, 1997 now allowed, all of which are incorporated by reference. The molecules can also be used to mediate the role of IL-9 in these and other conditions. To elaborate, since IL-9 induces TIFs, the TIFs are useful as IL-9 activity IL-6 mediators. Thus, a further aspect of the invention is a method to determine activity of endogenous IL-9, such as in situations where excess IL-9 activity is implicated, such as asthmas, allergies, and lymphomas. One can also block or inhibit IL-9 activity by blocking or inhibiting TIF or TIF activity, using, e.g., antisense molecules, antibodies which bind to TIF, or other antagonists of these molecules. The ability to regulate IL-9 activity is important in conditions such as those listed supra, as well as conditions such as apoptosis, including cortisol induced apoptosis, conditions involving the nuclear expression of BCL-3, since IL-9 is known to induce such expression, and so forth. "Antibodies," as used herein, refers to any portion of an antibody which binds to TIF, including chimeric and humanized antibodies.

Other features of the invention will be clear to the artisan and need not be discussed further.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated T cell inducible factor, the amino acid sequence of which is set forth at SEQ ID NO: 27 or 28.

2. The isolated T cell inducible factor of claim 1, having the amino acid sequence set forth at SEQ ID NO: 27.

3. The isolated T cell inducible factor of claim 1, having the amino acid sequence set forth at SEQ ID NO: 28.

* * * * *

UNITED STATES PATENT AND TRADEMARK OFFICE
CERTIFICATE OF CORRECTION

PATENT NO.    : 6,359,117 B1
DATED         : March 19, 2002
INVENTOR(S)   : Dumoutier et al.

Page 1 of 1

It is certified that error appears in the above-identified patent and that said Letters Patent is hereby corrected as shown below:

Drawings,
In the first line of amino acids marked "hTIF," change the amino acid at position 150 from "N" to -- D --.

Signed and Sealed this

Third Day of December, 2002

JAMES E. ROGAN
*Director of the United States Patent and Trademark Office*

SEQUENCE LISTING

```
<160> NUMBER OF SEQ ID NOS: 29

<210> SEQ ID NO 1
<211> LENGTH: 24
<212> TYPE: DNA
<213> ORGANISM: Mus musculus
<220> FEATURE:

<400> SEQUENCE: 1
agcactctcc agcctctcac cgca                                              24

<210> SEQ ID NO 2
<211> LENGTH: 12
<212> TYPE: DNA
<213> ORGANISM: Mus musculus
<220> FEATURE:

<400> SEQUENCE: 2
gatctgcggt ga                                                           12

<210> SEQ ID NO 3
<211> LENGTH: 24
<212> TYPE: DNA
<213> ORGANISM: Mus musculus
<220> FEATURE:

<400> SEQUENCE: 3
accgacgtcg actatccatg aaca                                              24

<210> SEQ ID NO 4
<211> LENGTH: 12
<212> TYPE: DNA
<213> ORGANISM: Mus musculus
<220> FEATURE:

<400> SEQUENCE: 4
gatctgttca tg                                                           12

<210> SEQ ID NO 5
<211> LENGTH: 24
<212> TYPE: DNA
<213> ORGANISM: Mus musculus
<220> FEATURE:

<400> SEQUENCE: 5
aggcaactgt gctatccgag ggaa                                              24

<210> SEQ ID NO 6
<211> LENGTH: 12
<212> TYPE: DNA
<213> ORGANISM: Mus musculus
<220> FEATURE:

<400> SEQUENCE: 6
gatcttccct cg                                                           12
```

<210> SEQ ID NO 7
<211> LENGTH: 1119
<212> TYPE: DNA
<213> ORGANISM: Mus musculus
<220> FEATURE:

<400> SEQUENCE: 7

| | | | | | |
|---|---|---|---|---|---|
| taaacaggct | ctcctctcac | ttatcaactg | ttgacacttg | tgcgatctct | gatggctgtc | 60 |
| ctgcagaaat | ctatgagttt | ttcccttatg | gggactttgg | ccgccagctg | cctgcttctc | 120 |
| attgccctgt | gggcccagga | ggcaaatgcg | ctgcccgtca | acaccggtg | caagcttgag | 180 |
| gtgtccaact | tccagcagcc | gtacatcgtc | aaccgcacct | ttatgctggc | caaggaggcc | 240 |
| agccttgcag | ataacaacac | agacgtccgg | ctcatcgggg | agaaactgtt | ccgaggagtc | 300 |
| agtgctaaag | atcagtgcta | cctgatgaag | caggtgctca | acttcaccct | ggaagacgtt | 360 |
| ctgctccccc | agtcagacag | gttccagccc | tacatgcagg | aggtggtacc | tttcctgacc | 420 |
| aactcagca | atcagctcag | ctcctgtcac | atcagcggtg | acgaccagaa | catccagaag | 480 |
| aatgtcagaa | ggctgaagga | gacagtgaaa | aagcttggag | agagtggaga | gatcaaggcg | 540 |
| attggggaac | tggacctgct | gtttatgtct | ctgagaaatg | cttgcgtctg | agcgagaaga | 600 |
| agctagaaaa | cgaagaactg | ctccttcctg | ccttctaaaa | agaacaataa | gatccctgaa | 660 |
| tggactttt | tactaaagga | aagtgagaag | ctaacgtcca | tcatcattag | aagatttcac | 720 |
| atgaaacctg | gctcagttga | aaagaaaat | agtgtcaagt | tgtccatgag | accagaggta | 780 |
| gacttgataa | ccacaaagat | tcattgacaa | tatttttattg | tcactgatga | tacaacagaa | 840 |
| aaataatgta | ctttaaaaaa | ttgtttgaaa | ggaggttacc | tctcattcct | ttagaaaaaa | 900 |
| agcttatgta | acttcatttc | catatccaat | attttatata | tgtaagttta | tttattataa | 960 |
| gtatacattt | tatttatgtc | agtttattaa | atgggattta | tttatagaaa | cattatctgc | 1020 |
| tattgatatt | tagtataagg | caaataatat | ttatgacaat | aactatggaa | acaagatatc | 1080 |
| ttaggcttta | ataaacacat | ggatatcata | aaaaaaaaa | | | 1119 |

<210> SEQ ID NO 8
<211> LENGTH: 7445
<212> TYPE: DNA
<213> ORGANISM: Mus musculus
<220> FEATURE:

<400> SEQUENCE: 8

| | | | | | |
|---|---|---|---|---|---|
| gtctatcacc | tgcttaagat | tcttctaatt | tataaaaaa | actatttctt | aaaatgaaaa | 60 |
| gcaaccagag | cacgtatta | tagcatggtg | ttctgaccat | gcaggtacag | agtggaatgg | 120 |
| taagaggcgc | tattatcagc | attaaccaac | atgttaatgt | tttcttctgg | caagcaaact | 180 |
| tgaaatctat | gtcttaaaca | atcttcaagc | ctctaatata | gtgctaacga | ctggagtccg | 240 |
| ctgctgtcca | acagagctct | tgagcacgct | ctcctctgtt | tgcaattta | tgttctttga | 300 |
| tcgactccca | aacctctcac | cttcggctcc | tgatggccac | ctttcaactt | tctgcattta | 360 |
| tgaactccat | gttttaatct | ttttattaaa | atattcacac | aatcagtgtt | tgtgcaagtc | 420 |
| tgtttcaccc | acatgtatgt | ctgtgcacca | agtgctgcct | ggtgcttgtg | ggggcaagga | 480 |
| gcaggagagg | gtgccctggc | accggagtca | cggatggttg | tgagccacca | tgaggatgct | 540 |
| gggagttaga | cccaggtcct | ccagaagtgc | agcaaatgct | cttaaccaca | cgcaggcatt | 600 |
| tctctctcca | gccccaacat | gagtgctttt | agattccacc | tagaatagag | atctgatggc | 660 |

-continued

| | |
|---|---|
| ttcactcact gccacctccc ctttgcatct ttctgccaag gaacaccaaa aagcaagaat | 720 |
| ccccacactg ctttcgctcc tcaagtctgc acctctcaac aggtcaagat tctccagtgt | 780 |
| ccctctaaca ctttccccag tgtccctcta acactttctc cagtgtccct ctaacacttt | 840 |
| ctccagtgtc cctctaacac ttttgatctc aattagctga ggggagaaag atctcacaca | 900 |
| gtgattttca tgacttcgcg ttctagtcta gatgtaggca tttgcgtgtc agtctagggt | 960 |
| aggcgtctgc tcccgctgct taggaaagac tttcctagtc tagttgtcag gtgctatctg | 1020 |
| ggattcagtg tacatacaat gcaaaaaatc ccagtatttt gtaaattctc ttcttcaact | 1080 |
| atccatctat atagtatgtt attgtaggct catttaaaaa taatattttg agacttatgc | 1140 |
| ttgcacaagt aaaatgtcag agaattagca aatgtatagt attattttat tttaaaaaaa | 1200 |
| tctatgctta aaatgtctat tagattgttc actaccgata tttccaaact taacttgacc | 1260 |
| ttggctatga tttcaacctt tgtatttgca tctaccataa cagtctctga accagaacat | 1320 |
| tctgtggcaa tgggagctgt gaagaaagcc aacattctta ttaaaaaaaa aaaacagcta | 1380 |
| gttatagttt aggattccat atactaaaaa aaatagagat ataattattt taaaaattga | 1440 |
| aataatctcc aagttttcat tatggcttat ttcaaagcac agaatatagg cacgggtct | 1500 |
| tttatttctg gtcacttcta aagagataag aatctatgaa gttggtggga aaatgagtcc | 1560 |
| gtgaccaaaa cgctgactca atagctacgg gagatcaaag gctgctctac tcaatcagaa | 1620 |
| tctactacgg caaagccatg gctttctttg aaaaccgtgt ttagaagatt tctgggattt | 1680 |
| gtgtgcaaaa gcaccttgtt ggccctcacc gtgacgtttt agggaagact tcccatctct | 1740 |
| caaggtggga aggcttggag gtggtgtctt gtggcctcct atggtggtta ggtacttctc | 1800 |
| agaagacagg actggaaatt agataatgtc tgatgtcata tcattcacaa taccaaaaaa | 1860 |
| accctggtgt cccgatggct ataaaagcag caacttctgc ctctcccatc acaagcagag | 1920 |
| acacctaaac aggtaagcac tcagacctct acagacaatc atctgcttgg taccatgcta | 1980 |
| cccgacgaac atgctcccct gatgttttg ccttttgctc tctcactaac aggctctcct | 2040 |
| ctcacttatc aactgttgac acttgtgcga tctctgatgg ctgtcctgca gaaatctatg | 2100 |
| agtttttccc ttatggggac tttggccgcc agctgcctgc ttctcattgc cctgtgggcc | 2160 |
| caggaggcaa atgcgctgcc cgtcaacacc cggtgcaagc ttgaggtgtc caacttccag | 2220 |
| cagccgtaca tcgtcaaccg cacctttatg ctggccaagg aggtacagct gcatctcttt | 2280 |
| ctctccatac cgccttgcca ttttctctga agcacttgca aactctttag gggcgcttta | 2340 |
| tctccgcagg tctcactacc tatgttttct gtctctttag agactcttta aggactgggt | 2400 |
| cttttttctat ttctatttca aggtctcagg accatttcct atcttggcct tcaggacaca | 2460 |
| tatactgaat tttatctaca gaggcgcatt tagaaagcca cccacgactg caatactttc | 2520 |
| catttctctg tgctctcttc tgaactcata tctctcttggc tactcctgag acccactgcg | 2580 |
| gacatacatc tctacttaca ggcttttctt ccatctcctt gtcacccagg cacttagggt | 2640 |
| tttctctctt tcaggccagc cttgcagata caacacaga cgtccggctc atcgggaga | 2700 |
| aactgttccg aggagtcagt gtaagtcctc actgtgatga gcaggctag ctgcgggagc | 2760 |
| tggtggaccc tctgggatag tctgacgtat gaccctgct gcttcttgtc tacctgcagg | 2820 |
| ctaaagatca gtgctacctg atgaagcagg tgctcaactt caccctggaa gacgttctgc | 2880 |
| tcccccagtc agacaggttc cagccctaca tgcaggaggt ggtacctttc ctgaccaaaac | 2940 |
| tcagcaatca gctcagctcc tgtgtaagtc tgactctggc tacctatgct cctctctctt | 3000 |
| cctcttctat tccagtaaga acccgaggtc ctgccctctc tctcttcaca agagtgagga | 3060 |

-continued

```
gggcctcagc accaccacca tcataggcca cttgaaatag gtcacaaagg ctttggcttc    3120
aattgagtaa tactttgagt ttgtatgagt gaagctttat ttgttttatc catggaaaga    3180
aatcaactca aattctgtag gatgagaaag atgttgggaa cgaaaaaagg cctagataga    3240
gaaacagatc tgctgagtat agtacttatg gggggagcag gggcgatat  ccactgagta    3300 caagtacttg tggggagaga atccactga gtacaagtac ttgttggcat ggagatccac     3360
tgagtacaag tacttgtggg ggagggaat ggcacagagc aaaagttgaa gggaaggaag     3420
atggagaggc ctcatggttg ggggtgtgaa aggtcactcc ttttccatgt gatggagagt    3480
taagaaaaac cagtgtgtga gtttgatgtc ttcagacacc cccaactatg aaacatatcc    3540
acgaggagcg ggcagactgt gggagacctg gcatttaggg aaggcgcggc ttttcacacg    3600
agaaacttta tgctcatctc ttgtgctaca ctcccacctt tgatgaggtt cagctcaggt    3660
ttcgtttcta ccgttcttgc tactggtgga aacttcagta ggattcccca agacgagga    3720 cagctcttct gtaagggagg gacctggatt tcagtgtcct agagaacgaa atagctcaga    3780
gaatctaggt caacgtgaaa tctaggtcac agcgggcaaa aatgactgaa cgcctctatt    3840
ccaggtgaac ggtcacgtgc ctcagatata ctgaggtatt gggctcccac cggataagat    3900
tctgttagtg agtctgcttt tattttgcag cacatcagcg gtgacgacca gaacatccag    3960
aagaatgtca gaaggctgaa ggagacagtg aaaaaggtac tattggcaag ccacaatact    4020
aagccattca gtaggagacg tggggatttc tttctctgct tcccagtccc ttctactttg    4080
taacatttta tttgacttgt ctactatctg gtccattact cgcttagctg cacctgtatc    4140
tagctgggtc tatagatctt tcaatctgtg tctaaatttg taagtcacaa ttctggagct    4200
agcagaaagc ttagctcagc cagtctcatg agcacttgct cggaggatgg cttgtgacag    4260
agtcaatgct agaagacagc atccctgatt cccagctctg cacttgccta gtggccatgt    4320
gtaattactt tggcttgatt aagtatttgg gaaagccagt tcccacggac ctacataatc    4380
tgaagaacca tgcattgaaa actagaaagc tgggcacaaa cttactagag atgattttg     4440 agctcattaa acggatgctc tgaaatgtgg caaaatcaac ccagaataac aacaaaagag    4500
ctggatttgc aaataggaca agtatttaga atcactggta ttaatagcta tcatcttaat    4560
taaaatatag ggcctatata tatatttaag attaaacaca agagtggata gcctcccaat    4620
ttacttggcc tggtttcaaa agagtaaaaa tatcagtcat ggattaatta tagtgtcatg    4680
aaagtatgag atggaaaccc ttttccttact ttttaccttc atttcttagt ttttttttc    4740 ttcacaccct gatcaagcca ctagtaagca cctatctgct gtgagctatt atatgacttt    4800
acagcaaaca acattgctgt gtggcctctt tggggaaggg aacaggatag caggaggctc    4860
aggctagcaa gtctgacttg ccctaaagcc agaggcatgg ttgatagcag agaaagtgag    4920
gctcttcgca agtgggtgtg cttaagtaat cagaaacagg aaggctccgg ttgatggaat    4980
tatcagtaag atatctaccc ttatctcctt ctatcgaacc taaatcgtct cttttcttg     5040 tgtgtaggct gataaacaca cttgtttct  tttgagtgtt catggctttg tagattttta    5100
gtgctctgcc agttcttgtt agagggtttg ttaccttgac acctgggctt ggatgttagc    5160
atgccaaagg cacacacttc tgaatgcctg tgtaaaaggt tattattcat ttactttgtc    5220
tttggaaagg tgaagcgtgt gtgagaaaga actcacagga gatgtgttct ctgtaggaaa    5280 acttttttt  tcccccttaaa tgcctataat ccactttcag tcaactttga cttttatacc    5340
atgctgtcac atgaaagagt gtttaggccc gctctcatgg ctctgggaaa agcaccaata    5400
```

-continued

```
ggggaaggaa tgttatgctg agaaatctga ccggcaggga aactggtcag agctcccccg   5460
aagaccacca caggtgttaa gtaggaacag tccagggtgg gctcatgtaa tagaatggaa   5520
cagagcgagg gaagataagc tacaaagttt catagggtcc ggagtcttaa agatacaaaa   5580
tagctgcttg ggcttcataa caaaggaagt ctgggaaggc agcaagtgag agggaaatgg   5640
aaagggaaaa aacagaatgt agaggacttg aacagctaca aatcctctac cagacgattt   5700
ttcttggaac aatctagaag gtagtggatt aggtgattgc aggggacttt gctttgccat   5760
ttgaatctgg gttttgtct ctccattgag gttgaaagcg tcacccttt taccctcgaa    5820 tggaggagga aagaagggt gttatgactc ctacctggag ttttactagt ttacgcaatg    5880
gaacagacac tcgggacctc ctcttgacaa aaaaaatgga aacctgttgt ttgtcttgtt   5940
tgttcttttg ttaagaaagc acaggcaaag cccgaccaca tgggttgaat gtgggtcttt   6000
gagtcaaggc ttttgagttg agcactcatc aatagttgat catggtcagg tggagggcta   6060
cctgtcaggc cgagccctgc tggcttcgca cttaacatct ccaggtctca gtatcacttc   6120
ctgctactta gcacagttag gagttgagca aaccttttt tccaaccccc actaaaattt    6180
aattgacaaa agactgtgta atttgtggga tacagtgtga taattgatct atgtgtgcat   6240
tgtgcaaggt tcaataagat agattaatag gcccatcaac agctttatgg gtgtgaaatg   6300
caagtaatat aggtagatgc ctgtggtgtc cttaggtcag aaaggcatga ttttaaggtc   6360
ttgggcaaat catattatac tcatgctaaa aatacattat gttgattatt aatcttttag   6420
agaaggctga tacttggttt tggtgctcag caagcaaatg tcaccagctc tttctaactg   6480
gtaccacttt agaaaatgct acctgtgctc aaattggttt gtattcttat tttcatagct   6540
tggagagagt ggagagatca aggcgattgg ggaactggac ctgctgttta tgtctctgag   6600
aaatgcttgc gtctgagcga aagaagcta gaaaacgaag aactgctcct tcctgccttc    6660 taaaagaac aataagatcc ctgaatggac ttttttacta aaggaaagtg agaagctaac    6720
gtccatcatc attagaagat ttcacatgaa acctggctca gttgaaaaag aaaatagtgt   6780
caagttgtcc atgagaccag aggtagactt gataaccaca aagattcatt gacaatattt   6840
tattgtcact gatgatacaa cagaaaaata atgtacttta aaaaattgtt tgaaaggagg   6900
ttacctctca ttccttaga aaaaaagctt atgtaacttc atttccatat ccaatatttt    6960
atatatgtaa gttatttat tataagtata cattttattt atgtcagttt attaatatgg    7020
atttatttat agaaacatta tctgctattg atatttagta taaggcaaat aatatttatg   7080
acaataacta tggaaacaag atatcttagg ctttaataaa cacatggata tcataaatct   7140
tctgtcttgt aattttctc cctttaatat caacaatacc atcatcatca tcattaccca    7200
atcattctca tgatttcatg cttgacccat attatactgt taaagttggt tcctggaggc   7260
ctgtggtttt gtgtgtgttg tgtgtgtgtg tggggttatg catgtgaaag ccagagatgg   7320
atattaggtg ttcttctcta tcagtctttg ccttattatt tgagacaggg tctgtcactg   7380
aacctgtagc taggctggcc aacaagctct attaattttt tttaagatta attaattatg   7440
tgtat                                                              7445
```

<210> SEQ ID NO 9
<211> LENGTH: 1111
<212> TYPE: DNA
<213> ORGANISM: Mus musculus
<220> FEATURE:

<400> SEQUENCE: 9

```
aacaggctct cctctcagtt atcaactttt gacacttgtg cgatcggtga tggctgtcct      60
gcagaaatct atgagttttt cccttatggg gactttggcc gccagctgcc tgcttctcat     120
tgccctgtgg gcccaggagg caaatgcgct gcccatcaac acccgtgca agcttgaggt     180 gtccaacttc cagcagccgt acatcgtcaa ccgcaccttt atgctggcca aggaggccag     240
ccttgcagat aacaacacag acgtccggct catcggggag aaactgttcc gaggagtcag     300
tgctaaggat cagtgctacc tgatgaagca ggtgctcaac ttcaccctgg aagacattct     360
gctcccccag tcagacaggt tccggcccta catgcaggag tggtgccttt cctgaccaa      420 actcagcaat cagctcagct cctgtcacat cagtggtgac gaccagaaca tccagaagaa     480
tgtcagaagg ctgaaggaga cagtgaaaaa gcttggagag agcggagaga tcaaagcgat     540
cggggaactg gacctgctgt ttatgtctct gagaaatgct tgcgtctgag cgagaagaag     600
ctagaaaacg aagaactgct ccttcctgcc ttctaaaaag aacaataaga tccctgaatg     660
gactttttta ctaaaggaaa gtgagaagct aacgtccacc atcattagaa gatttcacat     720
gaaacctggc tcagttgaaa gagaaaatag tgtcaagttg tccatgagac cagaggtaga     780
cttgataacc acaaagattc attgacaata ttttattgtc attgataatg caacagaaaa     840
agtatgtact ttaaaaaatt gtttgaaagg aggttacctc tcattcctct agaagaaaag     900
cctatgtaac ttcatttcca taaccaatac tttatatatg taagtttatt tattataagt     960
atacatttta tttatgtcag tttattaata tggatttatt tatagaaaaa ttatctgatg    1020
ttgatatttg agtataaagc aaataatatt tatgataata actatagaaa caagatatct    1080
taggctttaa taaacacatg aatatcataa a                                   1111

<210> SEQ ID NO 10
<211> LENGTH: 21
<212> TYPE: DNA
<213> ORGANISM: Mus musculus
<220> FEATURE:

<400> SEQUENCE: 10
ctgcctgctt ctcattgccc t                                                21

<210> SEQ ID NO 11
<211> LENGTH: 21
<212> TYPE: DNA
<213> ORGANISM: Mus musculus
<220> FEATURE:

<400> SEQUENCE: 11
caagtctacc tctggtctca t                                                21

<210> SEQ ID NO 12
<211> LENGTH: 20
<212> TYPE: DNA
<213> ORGANISM: Mus musculus
<220> FEATURE:

<400> SEQUENCE: 12
gacgcaagca tttctcagag                                                  20

<210> SEQ ID NO 13
<211> LENGTH: 16
<212> TYPE: DNA
<213> ORGANISM: Homo sapiens
<220> FEATURE:

<400> SEQUENCE: 13
```

```
atgtatttcc cagaaa                                              16

<210> SEQ ID NO 14
<211> LENGTH: 17
<212> TYPE: DNA
<213> ORGANISM: Homo sapiens
<220> FEATURE:

<400> SEQUENCE: 14 cctttctgg gaaatac                                              17

<210> SEQ ID NO 15
<211> LENGTH: 22
<212> TYPE: DNA
<213> ORGANISM: Homo sapiens
<220> FEATURE:

<400> SEQUENCE: 15
agctgctcaa cttcaccctg ga                                       22

<210> SEQ ID NO 16
<211> LENGTH: 22
<212> TYPE: DNA
<213> ORGANISM: Homo sapiens
<220> FEATURE:

<400> SEQUENCE: 16
ccactctctc caagcttttt ca                                       22

<210> SEQ ID NO 17
<211> LENGTH: 21
<212> TYPE: DNA
<213> ORGANISM: Homo sapiens
<220> FEATURE:

<400> SEQUENCE: 17
caagtctacc tctggtctca t                                        21

<210> SEQ ID NO 18
<211> LENGTH: 21
<212> TYPE: DNA
<213> ORGANISM: Homo sapiens
<220> FEATURE:

<400> SEQUENCE: 18
tggccaggaa gggcaccacc t                                        21

<210> SEQ ID NO 19
<211> LENGTH: 21
<212> TYPE: DNA
<213> ORGANISM: Homo sapiens
<220> FEATURE:

<400> SEQUENCE: 19
tggccaggaa gggcaccacc t                                        21

<210> SEQ ID NO 20
<211> LENGTH: 36
<212> TYPE: DNA
<213> ORGANISM: Homo sapiens
<220> FEATURE:
<221> NAME/KEY:
<222> LOCATION: 24,25,34,35
<223> OTHER INFORMATION: n is inosine
```

```
<400> SEQUENCE: 20
ggccacgcgt cgactagtac gggnngggnn gggnng                                36

<210> SEQ ID NO 21
<211> LENGTH: 20
<212> TYPE: DNA
<213> ORGANISM: Homo sapiens
<220> FEATURE:

<400> SEQUENCE: 21
ggccacgcgt cgactagtac                                                  20

<210> SEQ ID NO 22
<211> LENGTH: 20
<212> TYPE: DNA
<213> ORGANISM: Homo sapiens
<220> FEATURE:

<400> SEQUENCE: 22
ccttccccag tcaccagttg                                                  20

<210> SEQ ID NO 23
<211> LENGTH: 20
<212> TYPE: DNA
<213> ORGANISM: Homo sapiens
<220> FEATURE:

<400> SEQUENCE: 23
taattgttat tcttagcagg                                                  20

<210> SEQ ID NO 24
<211> LENGTH: 690
<212> TYPE: DNA
<213> ORGANISM: Homo sapiens
<220> FEATURE:

<400> SEQUENCE: 24
tgcacaagca gaatcttcag aacaggttct ccttccccag tcaccagttg ctcgagttag       60
aattgtctgc aatggccgcc ctgcagaaat ctgtgagctc tttccttatg gggaccctgg      120
ccaccagctg cctccttctc ttggccctct tggtacaggg aggagcagct gcgcccatca      180
gctcccactg caggcttgac aagtccaact tccagcagcc ctatatcacc aaccgcacct      240
tcatgctggc taaggaggct agcttggctg ataacaacac agacgttcgt ctcattgggg      300
agaaactgtt ccacggagtc agtatgagtg agcgctgcta tctgatgaag caggtgctga      360
acttcaccct tgaagaagtg ctgttccctc aatctgatag gttccagcct tatatgcagg      420
aggtggtgcc cttcctggcc aggctcagca acaggctaag cacatgtcat attgaaggtg      480
atgacctgca tatccagagg aatgtgcaaa agctgaagga cacagtgaaa agcttggag       540 agagtggaga gatcaaagca attggagaac tggatttgct gtttatgtct ctgagaaatg      600
cctgcatttg accagagcaa agctgaaaaa tgaataacta ccccctttc cctgctagaa       660 ataacaatta gatgccccaa agcgattttt                                       690

<210> SEQ ID NO 25
<211> LENGTH: 4797
<212> TYPE: DNA
<213> ORGANISM: Homo sapiens
<220> FEATURE:

<400> SEQUENCE: 25
```

-continued

| | | |
|---|---|---|
| tgcacaagca gaatcttcag aacaggttct ccttccccag tcaccagttg ctcgagttag | 60 |
| aattgtctgc aatggccgcc ctgcagaaat ctgtgagctc tttccttatg gggaccctgg | 120 |
| ccaccagctg cctccttctc ttggccctct tggtacaggg aggagcagct gcgcccatca | 180 |
| gctcccactg caggcttgac aagtccaact ccagcagcc ctatatcacc aaccgcacct | 240 |
| tcatgctggc taaggaggta tacatctcaa tcctgctctt tctcgttgga tctacttgga | 300 |
| atccaaatag ttcttaaact tttcttcaga gcatctctaa gagctttagg aacccactgt | 360 |
| ttatccctga gggtagataa attttctgtt ttttcagaga ctctttggga atctggcttt | 420 |
| ttttttttct tgaacttctt ccttccattt tggcctttat gatacatatg atgaattttt | 480 |
| cccaaagagc ggccattcag taatccatct gatgattttt ttttccttta tgcctctgtg | 540 |
| cattgttcta aactcatgca cacatctgaa ttctgctttt agtctttatg atgttgctct | 600 |
| ggggagacgg gatggggcac atgtctatgt ataaattttt tttctatttg ctcaatgtcc | 660 |
| agcccttag tcttttcttc tcttccaggc tagcttggct gataacaaca cagacgttcg | 720 |
| tctcattggg gagaaactgt tccacggagt cagtgtaagc tacagttgtg acgaacaggg | 780 |
| ccgtgtgccg tccatgggta cttggggtgg tggtgatgat ggtttaggtc ttatcccttta | 840 |
| tgaccctttc tgtttccctt ccacctgcag atgagtgagc gctgctatct gatgaagcag | 900 |
| gtgctgaact tcacccttga agaagtgctg ttccctcaat ctgataggtt ccagccttat | 960 |
| atgcaggagg tggtgccctt cctgccagg ctcagcaaca ggctaagcac atgtgtaagt | 1020 |
| tcagctctca gcctatgccc acctacccct ccttccctcc ttccacagag acccccttac | 1080 |
| cccaactctc tctccttccc cctaccccta agctagcagg aagaagtgtc ttggcagcag | 1140 |
| tgttatcagg agtcatttgg gatcatagag tatttgcttt tgctttgact gagtcacatc | 1200 |
| ttgagtttat agtggtgaat ggggtctgga acttaagtgt acagaagccg cattggtttg | 1260 |
| tcttcggaaa aaggcaact caggttgcgt aagatgagaa aggtgttggg aaaacatcta | 1320 |
| gctgtggaaa tggatccatt gagtctaagt tgttgagggg aggggatggc atggagagaa | 1380 |
| attagaagag aaagtgggaa atgggaaggc ttaaagtcgg tggtgggtcg gcagactgtt | 1440 |
| gccctgttga tgtcatggga agccacaaaa tcggaggcgt gtgaacttga tgccgctgaa | 1500 |
| catttgaaac tatgaaaaaa agtttgagtg gagtgggccc agtaaaaggc cctaggactt | 1560 |
| actgaagagg gcttaatttt cacatgagat gttttatgta catttcttgt tctaagcatg | 1620 |
| caattttctg gagatacgat tgaggtttta ttccttacag aatttgcata aactactccg | 1680 |
| ctctttccac aaatgcaaac ctcagtagga tttcccaaag atgaagagag gtctcttgta | 1740 |
| agggaagtga ctggattctg gcgtccaagg gaattcaaga gctcaggaaa tctaggtcac | 1800 |
| tgttgaaatc taggtcattg tgggcaaaat tactaagagc tttaattcca ggtgaattgt | 1860 |
| actgtacctc catgggtgtg gaggttcata aagtttcagc acaacattaa gatagttatg | 1920 |
| cttgttattg ttttatagca tattgaaggt gatgacctgc atatccagag gaatgtgcaa | 1980 |
| aagctgaagg acacagtgaa aaaggtagga ctgataactg tcaatgctaa gtcatgcaat | 2040 |
| aggagagaca aatgttgttt ttctttcctt tctttcttcc catcactttg tgattttttca | 2100 |
| cttgattctc ctaccaccag ggcgattact ttggtgtctg tgtatgtaga tatatctata | 2160 |
| tatctagatg tcagtttcca aatcttgcaa attgtagaat tctagaactg gttgggatct | 2220 |
| tagcttgtct agtcacataa cctcagattc tggggatggt cagtggcaga gatagggcta | 2280 |
| gaatgcaggt ctcctgaatc ccaagccagc acttttcccg gtggtgatac agattagttt | 2340 |
| tggtaccatt aattcttagg gaaatttcag attcctattg actcatgtaa tctgaagaag | 2400 |

```
tacttgttta aaaacagaaa aatgcctatg ggcaaattta tttgaagtca tttttgaagt    2460
cattaatgca ttgctttgaa acttggaaga ataaactcag aacaatgaga aaagagctgg    2520
acttgcatat agggctaatt tctggagtaa taaacactta ttttgaatta tcataatatc    2580
tatcagatat tgattatagt ttaaaagcaa gagcagacaa ccccgatctc ttttatacag    2640
gttcaaatag agtaaaaata ttagtaagag atttattata gttaaatgga agtctgaatt    2700
ggtaagcttt ttttcttcc tctctcccat caagaccttc cattctagtt tcttccttca     2760
ctccctcaac aaatccctag ggagcattta tccatggtgg gctggtgtac atttctatag    2820
tgaatgatac catcatgtgg cctatttggt gaaagaaca acaatggaag gcttagacta     2880
acaatagtga ctcaccccaa aaccggagga atgattagga gcagtgaaag tgacgctctt    2940
gcaagcaggt acaactaaat actcagaaac atgaaggctc cagttgatgg aattttcagt    3000
aacaagctta accttaattc cccctttttc cctcttgact ttttaaaaaa gcgtttcttc    3060
ctgagcatca tttaatgagt gtgactgttt cttcctttga taattgaagg ctttgtagtt    3120
ttaaattgtg aagcccagtt ctcttgttat agaactatta tctagacatg gagggctgaa    3180
tgttagcatg ccacagacaa ggcatgcttt acacatcttg cttaaaaaat tactgatttc    3240
atcttgcttg ttgtctttag aaaagtgaag tgtgagagag gagaatctca tggtgatctg    3300
tgtgattttc aagacctttta atccatttg aaagaatcaa tttcatattt gcaatgggtt    3360
gccatgtgga agagtgatta tgctttttg ctggtagctt cagaaagcac aggagggaga    3420
gcaatgttgt tcagagaaag atcaacagga ggagaaactg tcagagctgt ctgaaatagg    3480 gtggtttttgg gaggcattaa ttccctctcg ttgggggtaa aagcagaacg caggttggta    3540
gtaaaatgca tgacagacag taggggacga taaactttaa aattctttat agtcttggag    3600
tctttgagat agaaaagaat atcttttttgg ccttatgtca aaagaagtat ggaaaggtga    3660
aagggcggaa gaaagcagga aaaggaagaa ccatgtatta tatagaggac aatggtgaca    3720
aggtttttct tgaaataatg caaatatgat agattagagg aatttcagta gggaatgctt    3780
ttcacttgaa tttgggttttc ctcttcgatt aagtttggga tcctcatctg catttgactt    3840
ggagagagaa agaatgaatg ttaggaccta tatctggttt tctattaact aaagcaagtg    3900
gaaaagactt atttggtatt tttcccacaa aagtgaaaac ttttctttta ctgtttgtca    3960
aaaaggtgga aatagaaaaa gccttaatgt attggtgaat acatggttca aagtcatttg    4020
agtagagatg ttttaaatca ggagtgtcca atcatttggc ttccctggac caccttgaaa    4080
gaattgtctt ggtacacaca taaaatacaa gaacaatagc tgatgagcta aaaaagtcca    4140
tgcataaatc tcatactgtt ttaagaaagt ttatgaattt ctgttagggt gcattcaaag    4200
ctgtcctggg ccatgtgcgg cctgtgggct gcaggttgga caagctcctt ataagtaatc    4260
tgtcatagat agttttggag ctgcaaaaca ggccaaggca taatgggtgg cactcgggat    4320
cccccagatc ccagcctcac ttcagtctcc ttgctctggt taagaagggg tggtcaactc    4380
tctgcccagc ttttaaacag cttcattagt gtgaggtgca cctgaaattg atgcctgctg    4440
gtggcctctc agtccagaga gccgtcattt taagctcttt ggcaaatcat acaatactaa    4500
agggatatta ctatgaatgt tttacaaatg cttaaaactc ggtttctgtc tccatcaacc    4560
taatcttgca atttctaatt tgttcacttt agaaaacatg gcataaatgc tcaaatactt    4620
ttgcattctt attttcacag cttggagaga gtggagagat caaagcaatt ggagaactgg    4680
atttgctgtt tatgtctctg agaaatgcct gcatttgacc agagcaaagc tgaaaaatga    4740
```

-continued ataactaacc ccctttccct gctagaaata acaattagat gccccaaagc gattttt        4797

<210> SEQ ID NO 26
<211> LENGTH: 20
<212> TYPE: DNA
<213> ORGANISM: Homo sapiens
<220> FEATURE:

<400> SEQUENCE: 26
atcagatgga ttactgaatg                                                  20

<210> SEQ ID NO 27
<211> LENGTH: 179
<212> TYPE: PRT
<213> ORGANISM: Mus musculus
<220> FEATURE:

<400> SEQUENCE: 27

Met Ala Val Leu Gln Lys Ser Met Ser Phe Ser Leu Met Gly Thr Leu
1               5                  10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val

<210> SEQ ID NO 28
<211> LENGTH: 179
<212> TYPE: PRT
<213> ORGANISM: Homo sapiens
<220> FEATURE:

<400> SEQUENCE: 28

Met Ala Ala Leu Gln Lys Ser Val Ser Ser Phe Leu Met Gly Thr Leu
1               5                  10                  15

Ala Thr Ser Cys Leu Leu Leu Leu Ala Leu Leu Val Gln Glu Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe

```
         65                  70                  75                  80
His Gly Val Ser Met Ser Glu Arg Cys Tyr Leu Met Lys Gln Val Leu
                     85                  90                  95

Asn Phe Thr Leu Glu Glu Ile Leu Phe Pro Gln Ser Asp Arg Phe Arg
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Cys Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 29
<211> LENGTH: 5935
<212> TYPE: DNA
<213> ORGANISM: Homo sapiens
<220> FEATURE:

<400> SEQUENCE: 29
```

| | | | | | |
|---|---|---|---|---|---|
| gaattcaagt | ccacatgcaa | tcaatccgaa | tactttgtaa | attctcttct | tcaaatatcc | 60 |
| atctatatag | tataagttat | tgtaggatca | tttaaaaata | atgttttgag | acttatgttt | 120 |
| gcacaagtaa | aatgtcagag | agaattagca | aatgtatagt | attattttat | tttaaaaaat | 180 |
| ctatgcttaa | aatgtctatt | agattgttca | ctactgacat | ttccaaactt | aacttgacct | 240 |
| tggctatgat | ttcaaccttt | gtatttgcat | ctaccataac | tgtgtgctca | cttaccatgc | 300 |
| tatccgacga | gcatgttccc | ctgatgtttt | tgccttttgc | tctctcgcta | acaggctctc | 360 |
| ctctcagtta | tcaacttttg | acacttgtgc | gatcggtgat | ggctgtcctg | cagaaatcta | 420 |
| tgagttttttc | ccttatgggg | actttggccg | ccagctgcct | gcttctcatt | gccctgtggg | 480 |
| cccaggaggc | aaatgcgctg | cccatcaaca | cccggtgcaa | gcttgaggtg | tccaacttcc | 540 |
| agcagccgta | catcgtcaac | cgcacccttta | tgctggccaa | ggaggtacag | ctgcatctct | 600 |
| ttctctccat | accgccttgc | catttctctg | aagcacttgc | aaactcttta | gggcgctttt | 660 |
| atctccgcag | gtctcactac | ctatgttttc | tgtctctttta | gagactcttt | aaggactgga | 720 |
| tctttttcta | tttctatttc | aaggtctcag | gaccatttcc | tatcttggcc | ttcaggacac | 780 |
| atatactgaa | ttttatctac | agaggcgcgt | ttagaaagcc | acccacgact | gcaatacttt | 840 |
| ccatcctgtt | gtgctctctt | ctgaactcat | actctcttgg | ctactcctga | gacccactgc | 900 |
| ggacatacat | ctctacttac | aggcttttct | tccatctcct | tgtcacccag | gcacttaggg | 960 |
| ttttctctct | ttcaggccag | ccttgcagat | aacaacacag | acgtccggct | catcggggag | 1020 |
| aaactgttcc | gaggagtcag | tgtaagtcct | cactgtgatg | agcagggcta | gctgcgggag | 1080 |
| ctggtggacc | ctctgggata | gtctgacgta | tgacccctgc | tgcttcttgt | ctacctgcag | 1140 |
| gctaaggatc | agtgctacct | gatgaagcag | gtgctcaact | tcaccctgga | agacattctg | 1200 |
| ctcccccagt | cagacaggtt | ccggccctac | atgcaggagg | tggtgccttt | cctgaccaaa | 1260 |
| ctcagcaatc | agctcagctc | ctgtgtaagt | ctggctctgg | ctacctatgc | tcctctctct | 1320 |
| tcctcttcta | ttccagtaag | aacccgaggt | cctgccctct | ctctcttcac | aagagtgagg | 1380 |
| agggcctcag | caccaccacc | atcataggcc | acttgaaata | ggtcacaaag | gctttggctt | 1440 |

```
caattgagta atactttgag tttgtattag ttaagcttta tttgttttat ccatggaaag   1500
aaatcaactc aaattctgta ggatgagaaa gatgttggga acgaaaaaag gcctagatag   1560
agaaacagat ctgctgagta cagtacttat ggggggggg  ggcaggggc  gatatccact   1620 gagtccaagt acttgttggg agagaaatcc actgagtaca agtacttgtg ggggaaggaa   1680
tggcacagag caaaagttga agggaaagag gaagatggag aggcctcaat gttggggtg   1740 tgaaaggtca ctccttttc  catgtgatgg agagttaaga aaaatcagtg tgtgagtttg   1800
atgtcttcag acaccccaac tatggcagac tgtgggagac tggcattta  gggaaggcgc   1860 ggcttttcac acgagaaact ttatgctcat ctcttgtgct acactcccac ctttgatgag   1920
gttaagctca ggtttcgttt ctaccgttct tgctactggt ggaaacttca gtaggattcc   1980
ccaaagacga ggacagctct tctgtaaggg agggacctgg atttcagtgt cctagagaac   2040
gaaatagctc agagaatcta ggtcaacgtg aaatctaggt cacagcgggc aaaaatgact   2100
gaacgcctct attccaggtg aacggtcacg tgcctcagat atactgaggt attgggctcc   2160
caccggataa gattctgtta gtgagtctgc ttttattttg cagcacatca gtggtgacga   2220
ccagaacatc cagaagaatg tcagaaggct gaaggagaca gtgaaaaagg tactattggc   2280
aagccacaat actaagccat tcagtaggag acgtggggat ttctttctct gcttcccagt   2340
ctcttctact ttgtaacatt tcctttgact tgtctactgt ctggtccatt actcacttag   2400
ctgcacctgc atctagctgg gtctatagat ctttcaatct gtgtctaaat ttgtaagtca   2460
caattctgga gctagcagaa agcttagctc agccagtctc atgagcactt gctcggagga   2520
tggcttgtga cagagtcaat gctagaagac agcatccctg attcccagct ctgcacttgc   2580
ctagtggcca cgtgtaatta ctttagcctg attaagtatt tgggaaagcc aattcccacc   2640
gacctacata atccgaagaa gcatgcattg aaaactagaa agctgggcac aaacttacta   2700
gagatgattt ttgagctcat taaactgatg ctctgaaatg tgatcaaatc aacccagaat   2760
aacaacaaaa gagctggatt tgcaaatagg acaagtattt agaatcactg gtattaacag   2820
ctgtcatctt aattaaaata tagtgtctat ttagctgcct attaagatt  aaacacaaga   2880 gtggataact tcccaatttta ctgggcctgg tttcaataga gtaaaaatat cagtcataga   2940
ttaattatag tgtcatgaaa gtatgagttg gaaacccttt ccttactttt taccttcatt   3000
tcttagttat tatttttttt tcttcacacc ctgatcaagc cactagtaag cacctatctg   3060
ctgcgagcta ttatatgact ttacagcaaa caacattgct gtgtggcctc tttggggaag   3120
ggaacaggat agcaggaggc tcaggctagc aagtctggac tcaacctaaa gccagaggca   3180
tggttgatag cagagaaagt gaggctcttc acaagtgggg gtgcttaagt aatcagaaac   3240
aggaaggctc tggttgatgg aattatcagt aagatatcta cccttatctc cttcttctat   3300
agaagctaaa ccgtctctcc ttcttgtgtg taggctgata aacacgcttg ttttcttttg   3360
agtgttcatg gctttgcaga ttttcagtgc tctgccagtt cttgttagag ggtttgttac   3420
cttgacacct gggcttggat gttagcatgc caaaggcaca cacttctgaa tgcctgtgta   3480
aaaggttatt attcatttac tttgtctttg gaaaggtgaa gtgtgtgtga gaaagaactc   3540
acaggagatg tattctctgt aggaaaactt ttttttcccc ttaaaagcct ataatccact   3600
ttcagtcaac tttgacttt  ataccatgct gtcacatgaa agagtgttta ggcccgctct   3660
cgtggctctg ggaaaagcac caataggga  agaaatgtta tgccgagaaa tctgactggc   3720
agggaaactg ggtcagagct ccccaaagac cactacaggt gttaagtagg aacagtcgag   3780
ggtgggttca tataatagaa tggaacagag ggagggaaga taagctacaa agtttcatag   3840
```

-continued

```
ggtcctaagt ctttaagata caaaatagct ggttgggctt cataacaaag gaagtctggg      3900
aaggcagcaa gcattgagag ggagatggaa agggaaaaaa caatgtagag gatttgaaaa      3960
gctacaaatc ctccacgaga ggattttct tggaggaatc tagaacaagg gtggtggatt       4020
aggtggatcg cagaaggact tgctttgcca tttgaatctg ggttttgtc tctccattga       4080 ggttgagagc gtcacccttt tttaccctgg ataggaggag gaaagaaggg gtgttttgac      4140
tcctacctgg agttttacta gtttacgcaa tggaacagac actcgggacc tcctcttgac     4200 aagaaaaaa aaaaaaaag gaaacctgtt gtttctcttg tttgttcttt tgttaagaaa        4260
gcacaggcag ctgggcatgg tggcccatgc ctttaatccc agcatttggg aggcagaggc      4320
aggtgacttt ctaaattcaa ggccagcctg gtctacaaag tgagttccag gacagccagg      4380
gctatacaga gaaaccctgt ctcgggaaaa aaaaaaaga agaaaagaaa agaaaagaag       4440
agaagaggag aggagaggag aggagaggag aggagaggag aggagaggag aggagaggag      4500
aggagaggag aagagaagag aagagaagag aagagaagag aagagaagag aagagaagag     4560
aagagaagag aagagaagag aagagaagag aagagaagag aagagaaaag aaaagagaaa     4620
agaaaagaaa aaagcaagca agcaagcact ggcaaagcat gcccacatgg gacgtatgtg      4680 ggtcttgag acaaggcttt tgaattgagc gctcatcaat agttgatcat ggtcaggtgg       4740
agggctacct gtcaggccga gccctgctgg cttagcactt aacatctcca ggtctcagta     4800
tcacttcctg ctgcttagca cagttaggag ttgagcaaac cttttttcc aaccccact        4860 aaaatttaat ttacaaaagg cagtgtaatt tgtgggatac agtgtgataa ttgatctatg     4920
tgtgcattgt gcaaggttca ataaggtaga tcaataggcc catcaacagc tttatgggtg     4980
tgaaatgcaa gtaatatagg tagatgcctg tgtgtcctta ggtcagaaag gcatgatttt     5040
aaggtcttgg gcaaatcata ttatactcat gttaaaaatg cattatgttg attatcaatc     5100
ttttagagaa ggctgatact tggttttggt gctcagcaag caaatgtcac cagctctttc     5160
taactagtac cactttagaa aatgctaccc gtgctcaaat tggtttgtat tcttattttc      5220
atagcttgga gagagcggag agatcaaagc gatcggggaa ctggacctgc tgtttatgtc     5280
tctgagaaat gcttgcgtct gagcgagaag aagctagaaa acgaagaact gctccttcct     5340
gccttctaaa aagaacaata agatccctga atggactttt ttactaaagg aaagtgagaa     5400
gctaacgtcc accatcatta gaagatttca catgaaacct ggctcagttg aaagagaaaa     5460
tagtgtcaag ttgtccatga gaccagaggt agacttgata accacaaaga ttcattgaca    5520
atattttatt gtcattgata atgcaacaga aaaagtatgt actttaaaaa attgtttgaa    5580
aggaggttac ctctcattcc tctagaagaa aagcctatgt aacttcattt ccataaccaa    5640
tactttatat atgtaagttt attttattata agtatacatt ttatttatgt cagtttatta    5700
atatggattt atttatagaa aaattatctg atgttgatat ttgagtataa agcaaataat    5760
atttatgata ataactatag aaacaagata tcttaggctt taataaacac atgaatatca    5820
taaatcttct gtcttgtaat ttttctccct ttaatatcaa caataccatc atcgtcatca    5880
ttacccaatc attctcatga cttcatgctt gactcatatt atctggtaaa gtttg          5935
```